US009034863B2

(12) United States Patent
Uprichard et al.

(10) Patent No.: US 9,034,863 B2
(45) Date of Patent: May 19, 2015

(54) COMPOSITIONS AND METHODS FOR INHIBITING ENTRY OF A HEPATIC VIRUS (71) Applicant: The Board of Trustees of the University of Illinois, Chicago, IL (US)

(72) Inventors: Susan L. Uprichard, Chicago, IL (US); Bruno Sainz, Jr., Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/847,243

(22) Filed: Mar. 19, 2013

(65) Prior Publication Data
US 2013/0209401 A1 Aug. 15, 2013

Related U.S. Application Data (63) Continuation-in-part of application No. 13/061,598, filed as application No. PCT/US2009/055575 on Sep. 1, 2009, now Pat. No. 8,673,288.

(60) Provisional application No. 61/169,899, filed on Apr. 16, 2009, provisional application No. 61/093,549, filed on Sep. 2, 2008.

(51) Int. Cl.
*A01N 43/00* (2006.01)
*A61K 31/397* (2006.01)
*A61K 38/21* (2006.01)
*A61K 38/12* (2006.01)
*A61K 45/06* (2006.01)
*A61K 31/7068* (2006.01)

(52) U.S. Cl.
CPC .............. *A61K 31/397* (2013.01); *A61K 38/21* (2013.01); *A61K 38/215* (2013.01); *A61K 38/212* (2013.01); *A61K 38/12* (2013.01); *A61K 45/06* (2013.01); *A61K 31/7068* (2013.01)

(58) Field of Classification Search
None
See application file for complete search history.

(56) References Cited

U.S. PATENT DOCUMENTS

| 6,933,292 B2 | 8/2005 | Schaffner et al. | 514/210.02 |
| 7,098,198 B2 | 8/2006 | Schaffner et al. | 514/171 |
| 2008/0161324 A1 | 7/2008 | Johansen et al. | 514/255.03 |

OTHER PUBLICATIONS

Agnello et al. "Hepatitis C Virus and Other Flaviviridae Viruses Enter Cells via Low Density Lipoprotein Receptor" Proc. Natl. Acad. Sci. USA 1999 96(22):12766-12771.
Aizaki et al. "Critical Role of Virion-Associated Cholesterol and Sphingolipid in Hepatitis C Virus Infection" Journal of Virology 2008 82(12):5715-5724.
Barth et al. "Cellular Binding of Hepatitis C Virus Envelope Glycoprotein E2 Requires Cell Surface Heparan Sulfate" The Journal of Biological Chemistry 2003 278(42):41003-41012.
Barth et al. "Viral and Cellular Determinants of the Hepatitis C Virus Envelope-Heparan Sulfate Interaction" Journal of Virology 2006 80(21):10579-10590.
Bartosch et al. "Infectious Hepatitis C Virus Pseudo-particles Containing Functional E1-E2 Envelope Protein Complexes" The Journal of Experimental Medicine 2003 197(5):633-642.
Bays et al. "Ezetimibe: Cholesterol Lowering and Beyond" Expert Review of Cardiovascular Theory 2008 6(4):447-470.
Blanchard et al. "Hepatitis C Virus Entry Depends on Clathrin-Mediated Endocytosis" Journal of Virology 2006 80(14):6964-6972.
Evans et al. "Claudin-1 is a Hepatitis C Virus Co-receptor Required for a Late Step in Entry" Nature 2007 446(7137):801-805.
Garcia-Calvo et al. "The Target of Ezetimibe is Niemann-Pick C1-Like 1 (NPC1L1)" Proc. Natl. Acad. Sci. USA 2005 102(23):8132-8137.
Garry, R.F. and Dash, S. "Proteomics Computational Analyses Suggest that Hepatitis C Virus E1 and Pestivirus E2 Envelope Gylcoproteins are Truncated Class II Fusion Proteins" Virology 2003 307(2):255-265.
Gupta, E.K. and Ito, M.K. "Ezetimibe: The First in a Novel Class of Selective Cholesterol-Absorption Inhibitors" Heart Disease 2002 4(6):399-409.
Kapadia et al. "Initiation of Hepatitis C Virus Infection is Dependent on Cholesterol and Cooperativity between CD81 and Scavenger Receptor B Type I" Journal of Virology 2007 81(1):374-383.
Labonté et al. "Class B Type I Scavenger Receptor is Responsible for the High Affinity Cholesterol Binding Activity of Intestinal Brush Border Membrane Vesicles" Biochimica et Biophysica Acta 2007 1771(9):1132-1139.
Liu et al. "Tight Junction Proteins Claudin-1 and Occludin Control Hepatitis C Virus Entry and Are Downregulated During Infection to Prevent Superinfection" Journal of Virology 2009 83(4):2011-2014.
Meertens et al. "Hepatitis C Virus Entry Requires a Critical Postinternalization Step and Delivery to Early Endosomes via Clathrin-Coated Vesicles" Journal of Virology 2006 80(23):11571-11578.
Monazahian et al. "Low Density Lipoprotein Receptor as a Candidate Receptor for Hepatitis C Virus" Journal of Medical Virology 1999 57(3):223-229.
Pileri et al. "Binding of Hepatitis C Virus to CD81" Science 1998. 282(5390):938-941.
Ploss et al. "Human Occludin is a Hepatitis C Virus Entry Factor Required for Infection of Mouse Cells" Nature 2009 457(7231):882-886.
Saunier et al. "Role of the Asialoglycoprotein Receptor in Binding and Entry of Hepatitis C Virus Structural Proteins in Cultured Human Hepatocytes" Journal of Virology 2003 77(1):546-559.
Scarselli et al. "The Human Scavenger Receptor Class B Type I is a Novel Candidate Receptor for the Hepatitis C Virus" The EMBO Journal 2002 21(19):5017-5025.

(Continued)

*Primary Examiner* — Marcela M Cordero Garcia
(74) *Attorney, Agent, or Firm* — Licata & Tyrrell P.C.

(57) ABSTRACT

The present invention embraces Niemann-Pick C1-like 1 protein antagonists and agents that inhibit hepatic virus infection for use in the prevention and treatment of a hepatic virus infection.

5 Claims, 3 Drawing Sheets

(56) References Cited

OTHER PUBLICATIONS

Wünschmann et al. "Characterization of Hepatitis C Virus (HCV) and HCV E2 Interactions with CD81 and the Low-Density Lipoprotein Receptor" Journal of Virology 2000 74(21):10055-10062.

Office communication dated Aug. 12, 2013 from U.S. Appl. No. 13/061,598, filed Mar. 28, 2011.
International Search Report from PCT/US2009/055575, Oct. 15, 2009, PCT.
International Preliminary Report on Patentability from PCT/US2009/055575, Mar. 8, 2011, PCT.

COMPOSITIONS AND METHODS FOR
INHIBITING ENTRY OF A HEPATIC VIRUS

INTRODUCTION

This application is a continuation-in-part application of U.S. application Ser. No. 13/061,598, filed Mar. 28, 2011, which is the national phase under 35 U.S.C. §371 of PCT International Application No. PCT/US2009/055575, filed Sep. 1, 2009, which claims priority from U.S. Provisional Application Nos. 61/169,899, filed Apr. 16, 2009 and 61/093,549, filed Sep. 2, 2008, the contents of which are incorporated herein by reference in their entireties.

BACKGROUND OF THE INVENTION

Hepatitis C virus (HCV), a positive-strand RNA flavivirus, is a leading cause of liver disease worldwide. Although acute infection can be asymptomatic, approximately 80% of patients fail to clear the virus resulting in a chronic infection associated with significant liver disease, including steatosis, insulin-resistance, fibrosis, cirrhosis and hepatocellular carcinoma (Alter & Seeff (2000) *Semin. Liver Dis.* 20:17-35). As such, HCV-related cancer accounts for over 50% of hepatocellular carcinoma cases and over 30% of liver transplants performed in the United States. Despite this obvious public health burden, there is no vaccine to prevent infection.

HCV is thought to enter cells via receptor-mediated endocytosis beginning with binding of the viral particle to a series of cell surface receptors, including the tetraspanin CD81 (Pileri, et al. (1998) *Science* 282:938-41), the scavenger receptor class B member I (SR-BI) (Scarselli, et al. (2002) *EMBO J.* 21:5017-25) and the tight-junction proteins claudin-1 (Evans, et al. (2007) *Nature* 446:801-5) and occludin (Liu, et al. (2009) *J. Virol.* 83:2011-4; Ploss, et al. (2009) *Nature* 457:882-6), followed by clathrin-mediated endocytosis (Blanchard, et al. (2006) *J. Virol.* 80:6964-72; Meertens, et al. (2006) *J. Virol.* 80:11571-8) and class II fusion (Garry & Dash (2003) *Virology* 307:255-65) between the virion envelope and the endosomal membrane. Additionally, the low-density lipoprotein receptor (LDLR) (Agnello, et al. (1999) *Proc. Natl. Acad. Sci. USA* 96:12766-12771; Monazahian, et al. (1999) *J. Med. Virol.* 57:223-229; Wunschmann, et al. (2000) *J. Virol.* 74:10055-10062), asialoglycoprotein receptor (Saunier, et al. (2003) *J. Virol.* 77:546-559), protocadherin β5 (Womg-Staal, et al. (2008) 15th International Symposium on Hepatitis C Virus & Related Viruses. San Antonio, Tex.), and glycosaminoglycans (heparan sulfate) (Barth, et al. (2003) *J. Biol. Chem.* 278:41003-41012; Barth, et al. (2006) *J. Virol.* 80:10579-10590; Bartosch, et al. (2003) *J. Exp. Med.* 197:633-642) have been implicated; however, the role of those agents has not been conclusively proven to be essential for HCV entry. In addition, it has been shown that the HCV particle is not only uniquely enriched in cholesterol (Aizaki, et al. (2008) *J. Virol.* 82:5715-24), but that depletion of cholesterol ablates particle infectivity (Aizaki, et al. (2008) supra; Kapadia, et al. (2007) *J. Virol.* 81:374-83).

While clinically approved HCV entry inhibitors have not been identified, a number of agents have been described for inhibiting HCV replication. For example, the current treatment option for HCV is a combination therapy with interferon (IFN) and ribavirin. However, this combination has toxic side effects, marginal efficacy, and limited availability (Firpi & Nelson (2007) *Arch. Med. Res.* 38:678-690; Foster & Mathurin (2008) *Antivir. Ther.* 13:3-8). In addition, US 2008/0161324 describes a series of HCV replication inhibitors identified using a replication assay. However, the compounds identified therein were not shown to prevent infection and spread of HCV. As such, the identification of novel and more potent antivirals targeting other aspects of the viral life cycles (e.g., entry inhibitors) is imperative. In this respect, screening assays have been carried out for identifying agents or combinations of agents of use in treating viral infections (US 2008/0161324).

Ezetimibe, a 2-azetidinone class of drug, is an anti-hyperlipidemic, cholesterol-lowering medication, currently approved for use in humans by the U.S. Food and Drug Administration (FDA); the drug has been shown to potently inhibit cholesterol absorption in vivo, thus lowering plasma total and LDL cholesterol in treated individuals (Bays, et al. (2008) *Expert Rev. Cardiovasc. Ther.* 6:447-470). Data indicate that the protein known as Niemann-Pick C1-like 1 (NPC1L1) is the molecular target of ezetimibe in cells (Garcia-Calvo, et al. (2005) *Proc. Natl. Acad. Sci. USA* 102:8132-8137). Additional studies indicate that SR-B1 might be the target of ezetimibe action in cells (Labonte, et al. (2007) *Biochim. Biophys. Acta* 1771:1132-1139). Ezetimibe is marketed under the trade names EZETROL and ZETIA. It is also marketed in combination with the statin drug simvastatin (ZOCOR) under the trade names VYTORIN and INEGY. It is indicated as an adjunct to dietary measures in the management of hypercholesterolaemia, homozygous sitosterolemia (phytosterolemia), and the treatment of mixed hyperlipidaemia when used in combination with fenofibrate.

SUMMARY OF THE INVENTION

The present invention is a method for reducing or preventing entry of a hepatic virus by contacting the cell with an effective amount of a Niemann-Pick C1-like 1 (NPC1L1) protein antagonist. According to one embodiment of this method, the NPC1L1 antagonist is an azetidinone-based cholesterol absorption inhibitor. In particular embodiments, the azetidinone-based cholesterol absorption inhibitor is ezetimibe, or a derivative thereof.

The present invention also features a method for preventing a hepatic virus infection by administering to a subject in need of treatment an effective amount of a NPC1L1 antagonist so that entry of hepatic virus is reduced or prevented. According to one embodiment of this method, the subject has had a liver transplant. In another embodiment, the NPC1L1 antagonist is an azetidinone-based cholesterol absorption inhibitor. In particular embodiments, the azetidinone-based cholesterol absorption inhibitor is ezetimibe, or a derivative thereof.

A synergistic composition for treating a hepatic virus infection is also embraced by this invention. This synergistic composition is composed of a NPC1L1 antagonist and at least one other agent that inhibits hepatic virus infection. NPC1L1 antagonists particularly encompassed include azetidinone-based cholesterol absorption inhibitors, with particular embodiments drawn to ezetimibe, or a derivative thereof. In certain embodiments, the at least one other agent that inhibits hepatic virus infection is a type I interferon (IFN) such as IFN-α or IFN-β, a polymerase inhibitor such as RG7128 or a protease inhibitor such as ITMN-5537 or ITMN-191.

Another feature of this invention is a method for effecting clearance of hepatic virus from cells by contacting cells infected with a hepatic virus with an effective amount of the synergistic composition of the invention.

The present invention also embraces a method for treating a hepatic virus infection. This method involves administering to a subject with a hepatic virus infection an effective amount of the synergistic composition of the invention so that the hepatic virus infection is treated.

BRIEF DESCRIPTION OF THE DRAWINGS

FIG. 1 shows that ezetimibe inhibits HCV internalization, not binding. Monolayers of human hepatoma cell line Huh7 were inoculated with HCVcc JFH-1 (cell culture produced HCV JFH-1, which is a specific HCV clone isolated from a Japanese Fulminant Hepatitis patient) at an MOI of 0.1 FFU/cell for 6 hours in the presence or absence of increasing concentrations of ezetimibe. Cultures were washed extensively and cell associated RNA was collected 6 and 30 hours post-infection (p.i.) to determine the amount of bound and internalized virus, respectively. HCV RNA was quantified by RT-qPCR, normalized to GAPDH and is displayed as HCV RNA copies/μg total cellular RNA. Results are graphed as means±s.e.m. for triplicate samples. The data presented are representative of three independent experiments. Assay background (i.e., HCV RNA level detected in uninfected samples) is equal to ~0.5–1.0×$10^2$ copies/μg total cellular RNA. Significant reduction in HCV RNA levels relative to mock-treated cultures is denoted by a single asterisk (p<0.05, one-way ANOVA and Tukey's post hoc t test).

FIG. 2A, Cultures were mock treated, treated with ezetimibe alone (30 μM), IFN-α (100 U/ml) alone, or ezetimibe (30 μM) plus IFN-α (100 U/ml) in combination. Treatments were maintained as cultures were passaged. FIG. 2B, After 70 days IFN-α or combination ezetimibe plus IFN-α treatment, treatment was either continued (open shapes) or discontinued (filled shapes). Throughout the experiment, intracellular RNA was collected from an aliquot of cells from triplicate cultures on indicated days post-treatment and HCV RNA was quantified by RT-qPCR, normalized to GAPDH and is displayed as HCV RNA copies/μg total cellular RNA. Results are graphed as means±s.e.m. for triplicate samples. The data presented are representative of two independent experiments.

FIG. 4A, Chronically infected Huh7-1 cell cultures (n=3) treated with ezetimibe (E), naringenin (N), interferon α (I), or combinations thereof, were harvested at 24, 48, 72 or 96 hours post-treatment, intracellular HCV levels were quantified by RT-qPCR, and are presented as HCV copies/μg RNA. FIG. 4B, Chronically infected Huh7-1 cell cultures (n=3) treated with ezetimibe (E), ferristatin (T), interferon α (I), or combinations thereof, were harvested at 24, 48, 72 or 96 hours post-treatment, intracellular HCV levels were quantified by RT-qPCR, and are presented as HCV copies/μg RNA.

DETAILED DESCRIPTION OF THE INVENTION

It has now been shown that the clinically-available anti-cholesterol medication ezetimibe, which inhibits cellular cholesterol absorption (Gupta & Ito (2002) *Heart Dis.* 4:399-409), potently blocks HCV entry into cells, infection and cell-to-cell spread. Unlike statins that act intracellularly to limit cholesterol metabolism (e.g., by inhibiting the enzyme HMG-CoA reductase) thereby inhibiting HCV RNA replication or particle maturation (Kapadia & Chisari (2005) *Proc. Natl. Acad. Sci. USA* 102:2561-6; Sagan, et al. (2006) *Biochem. Cell. Biol.* 84:67-79; Ye, et al. (2003) *Proc. Natl. Acad. Sci. USA* 100:15865-70; Kapadia & Chisari (2005) Differential Regulation of HCV Genotype 1B and 2A RNA Replication by the Cholesterol and Fatty Acid Biosynthetic Pathways. In *12th International Symposium on Hepatitis C Virus & Related Viruses* (Montreal, Canada)), ezetimibe functions by preventing cholesterol and HCV particle internalization by antagonizing the Niemann-Pick C1-like 1 (NPC1L1) protein. Moreover, when used in combination with interferon, an HCV protease inhibitor ro an HCV polymerase inhibitor, ezetimibe synergistically cures chronically-infected cell cultures, reducing HCV RNA and protein to undetectable levels. Because ezetimibe is already approved for other clinical uses and has been found to be safe for patient use, one of skill will understand that the present invention could readily translate into a new, more effective, therapeutic treatment for a hepatic virus infection. Because it is involved in blocking viral entry into cells (i.e., not just inhibiting virus replication, but preventing viral infection) as well as cell-to-cell spread, ezetimibe and its derivatives can be used in the treatment of hepatic virus infection, e.g., to limit spread within the liver and to a new liver after liver transplantation, as well as in prophylactic treatment of healthcare workers or others at risk of a hepatic virus infection.

Accordingly, the present invention embraces the use of ezetimibe, as well as other agents that antagonize NPC1L1 or inhibit cellular cholesterol uptake, in methods for reducing or preventing entry of a hepatic virus into a cell, clearing a hepatic virus infection, and preventing or treating a hepatic virus infection and spread of virus, e.g., within in body or to a new liver after liver transplantation.

The term "hepatic virus" refers to a virus that can cause viral hepatitis. Viruses that can cause viral hepatitis include hepatitis A, hepatitis B, hepatitis C, hepatitis D, and hepatitis E. In addition, non-ABCDE cases of viral hepatitis have also been reported (see, for example, Rochling, et al. (1997) *Hepatology* 25:478-483). Within each type of viral hepatitis, several subgroupings have been identified. Hepatitis C, for example, has at least seven distinct genotypes (1, 2, 3, 4, 5, and 6), which have been further categorized into subtypes (e.g., 1a, 1b, 2a, 2b, 2c, 3a, 4a) (Simmonds (2004) *J. Gen. Virol.* 85:3173-3188). In particular embodiments of the invention, the hepatic virus is hepatitis C virus (HCV).

An NPC1L1 antagonist is used herein to refer to an agent that reduces the expression or activity, or inhibits expression or activity, of an NPC1L1 nucleic acid or polypeptide. Examples of antagonists include without limitation small molecules, anti-NPC1L1 antibodies, antisense nucleic acids, ribozymes, RNAi oligonucleotides, and molecules that target NPC1L1 promoter transcription factors. In particular embodiments, an NPC1L1 antagonist inhibits the activity of NPC1L1 by blocking internalization or uptake of a hepatic virus into cells. Specific NPC1L1 antagonists that inhibit NPC1L1 activity include, for example, azetidinone-based cholesterol absorption inhibitors (e.g., ezetimibe and its derivatives); 4-phenyl-4-piperidinecarbonitrile hydrochloride; 1-butyl-N-(2,6-dimethylphenyl)-2 piperidinecarboxamide; 1-(1-naphthylmethyl)piperazine; 3{1-[(2-methylphenyl)amino]ethylidene}-2,4(3H,5H)-thiophenedione, 3{1-[(2-hydroxyphenyl)amino]ethylidene}-2,4(3H,5H)-thiophenedione, 2-acetyl-3-[(2-methylphenyl)amino]-2-cyclopenten-1-one, 3-[(4-methoxyphenyl)amino]-2-methyl-2-cyclopenten-1-one, 3-[(2-methoxyphenyl)amino]-2-methyl-2-cyclopenten-1-one, and N-(4-acetylphenyl)-2-thiophenecarboxamide, or derivatives thereof. See, e.g., US 2009/0035784. In particular embodiments, the NPC1L1 antagonist is an azetidinone-based cholesterol absorption inhibitor. Azetidinone-based cholesterol absorption inhibitors are described, for example, by Rosenblum, et al. ((1998) *J. Med. Chem.* 41(6):973-80). A particularly preferred azetidinone-based inhibitor for use in compositions and methods of the present invention is ezetimibe (1-(4-fluorophenyl)-(3R)-[3-(4-fluorophenyl)-(3S)-hydroxypropyl]-(4S)-(4-hydroxyphenyl)-2-azetidinone) (also referred to in the literature as SCH 58235 or ZETIA) and its phenolic glucuronide derivative, SCH60663. See van Heek (2000) *Br. J. Pharmacol.* 129(8):1748-54. Additional ezetimibe-related derivatives for use in compositions and methods of the present invention are referred to in the literature as SCH 58053 or (+)-7-(4-chlorophenyl)-2-(4-flourophenyl)-7-hydroxy-3R-(4-hydroxyphenyl)-2-azaspiro[3,5]nonan-1-one) (Repa, et al. (2002) *J. Lipid Res.* 43:1864-1874); and SCH 48461 or (3R)-3 Phenylpropyl)-1,(4S)-bis(4-methoxyphenyl)-2-azetidinone (Salisbury, et al. (1995) *Atherosclerosis* 115:45-63). Moreover, NPC1L1 antagonists, e.g., small molecule antagonists, can be identified using conventional screening assays, which monitor cholesterol absorption or assays which monitor hepatic virus entry into a cell as described herein. Whether used alone or in combination with one or more agents, desirably the NPC1L1 antagonist is used in the range including, but not limited to, 10 to 50 µM.

According to one embodiment of the invention, an NPC1L1 antagonist is used in a method to reduce or prevent entry of a hepatic virus into a cell. This method involves contacting a cell with an NPC1L1 antagonist so that entry of a hepatic virus into a cell is reduced or prevented. In this respect an effective amount is an NPC1L1 antagonist in an amount which results in a 20% to 100% decrease in internalization, entry or uptake of a hepatic virus into a cell as compared to a cell not contacted with the NPC1L1 antagonist. Such a decrease in internalization can be determined using the techniques disclosed herein or any other suitable method for monitoring virus internalization, e.g., enzymatic reporter assays or monitoring intracellular localization by confocal microscopy. In particular embodiments of the present invention, the cell is a hepatic cell. In so far as entry of a hepatic virus into a cell is essential for establishing a hepatic viral infection, this method finds application in the preventing a hepatic virus infection in a subject.

Accordingly, another embodiment of the present invention embraces a method for preventing and/or treating hepatic virus infection by administering to a subject in need of treatment an effective amount of a NPC1L1 antagonist so that entry of a hepatic virus into cells is reduced or prevented thereby preventing and/or treating a hepatic virus infection. By "subject" is meant any animal (e.g., a mammal such as a human). As used herein, the term "hepatic virus infection" is used to describe the process of adherence and internalization of a hepatic virus, which is manifested by viral replication and viral persistence. Thus, "prevention" or "preventing" in the context of the present invention refers to prophylactic treatment which prevents or delays HCV-associated clinical symptoms. In this respect, subjects benefiting from prophylactic treatment with a NPC1L1 antagonist include, e.g., healthcare workers or others at risk of a hepatic virus infection, as well as hepatic virus-positive liver transplant patients, wherein prophylactic treatment prevents infection of the new liver.

In so far as the activity of ezetimibe was shown to synergize with the activity of various agents including interferons, protease inhibitors and polymerase inhibitors, the present invention also embraces a synergistic composition that includes a NPC1L1 antagonist in combination with at least one additional agent that inhibits hepatic virus infection (e.g., by inhibiting gene expression, replication, assembly, maturation, or release) for use in the treatment of a hepatic virus infection. A composition of the invention is deemed synergistic since the individual components, when combined, have a total effect that is greater than the sum of the individual effects. Suitable NPC1L1 antagonists are disclosed herein, with particular embodiments embracing azetidinone-based cholesterol absorption inhibitors such as ezetimibe or its derivatives. In this respect, NPC1L1 antagonists, as hepatic virus entry inhibitors, are distinct from replication inhibitors. Thus, according to one embodiment of the invention, the at least one additional agent that inhibits hepatic virus infection is an inhibitor of viral replication. Agents that inhibit hepatic virus replication are known in the art and can target a variety of different replication mechanisms. For example, HCV replication can be inhibited by reducing the rate of any of the steps required for its replication or inhibiting any molecule involved in replication, including but not limited to, viral genome replication, translation of viral RNA, and proteolytic processing. In some embodiments, agents of use in the compositions and methods of the invention inhibit one or more of a hepatic virus metalloprotease, serine protease, polymerase, helicase, NS4B protein, and NS5A protein. Examples of suitable agents include, but are not limited to, type I interferons (Zeuzem, et al. (1996) *Hepatology* 23(2):366-71); statins (Ikeda, et al. (2006) *Hepatology* 44(1):117-25); replication inhibitors such as iminothiazolidinones (U.S. Pat. No. 7,183, 302), ribavirin (Gish (2006) *J. Antimicrob. Chemother.* 57(1): 8-13), nucleoside analog R1479 (Klumpp, et al. (2006) *J. Biol. Chem.* 281(7):3793-9), substituted diphenyl heterocyclic compounds (e.g., R706 or R803, Huang, et al. (2008) *Antimicrob. Agents Chemother.* 52(4):1419-29) and bisindolylmaleimides and indolocarbazoles (Murakami, et al. (2009) *Antiviral Res.* 83:112-117); nucleoside inhibitor R1626 (Toniutto, et al. (2008) *IDrugs* 11(10):738-49); polymerase inhibitors such as beta-D-2'-Deoxy-2'-fluoro-2'-C-methylcytidine (PSI-6130 or its prodrug RG7128; Asif, et al. (2007) *Antimicrob. Agents Chemother.* 51(8):2877-82); protease inhibitors such as Telaprevir (Weisberg & Jacobson (2009) *Clin. Liver Dis.* 13(3):441-52; Serrazin, et al. (2007) *Gastroenterology* 132(5):1767-77), Boceprevir (Mederacke, et al. (2009) *Curr. Opin. Investig. Drugs* 10(2):181-9), ITMN-191 (danoprevir or R7227, Seiwert, et al. (2008) *Antimicrob. Agents Chemother.* 52(12):4432-41), and the structurally related inhibitor ITMN-5537; and combinations thereof. In some embodiments, the inhibitor is an HCV protease inhibitor. In other embodiments, the inhibitor is an HCV polymerase inhibitor. In particular embodiments, the synergistic composition does not include simvastatin.

ITMN-5537

ITMN-191

In certain embodiments, the synergistic composition of the invention includes an NPC1L1 antagonist and at least a type I interferon (e.g., IFN-α or IFN-β), ribavirin, or a combination thereof. In this respect, one embodiment embraces a synergistic composition composed of 1) a NPC1L1 antagonist, 2) a type I interferon or ribavirin, 3) and an additional agent that inhibits hepatic virus infection. As used herein, a type I interferon refers to the family of interferon proteins that inhibit viral replication, inhibit cellular proliferation, and modulate immune response. There are a variety of commercially available alpha interferons, including, but not limited to, Roferon A interferon (Hoffman-La Roche, Nutley, N.J.), Berofor alpha 2 (Boehringer Ingelheim Pharmaceutical, Inc., Ridgefield, Conn.), and Sumiferon (Sumitomo, Japan). Alpha interferon 2b currently has the broadest approval throughout the world for use in treating HCV. U.S. Pat. No. 4,530,901 provides a description of the manufacture of alpha interferon 2b. In a particular embodiment, the synergistic composition includes ezetimibe and IFN-α.

In certain other embodiments, the synergistic composition of the invention includes an NPC1L1 antagonist and at least one hepatic protease inhibitor. As indicated above, there are a variety of known hepatic protease inhibitors including, but not limited to, Telaprevir, Boceprevir, ITMN-191 (R7227, Danoprevir), and ITMN-5537, each of which are available from commercial sources. In a particular embodiment, the synergistic composition includes ezetimibe and ITMN-5537.

In yet other embodiments, the synergistic composition of the invention includes an NPC1L1 antagonist and at least one hepatic polymerase inhibitor. A number of polymerase inhibitors are known in the art and include, but are not limited to, beta-D-2'-Deoxy-2'-fluoro-2'-C-methylcytidine (PSI-6130) or its prodrug, RG7128 (mericitabine). In a particular embodiment, the synergistic composition includes ezetimibe and RG7128.

In some embodiments, the synergistic composition contains different amounts of each component. In this respect, certain embodiments of this invention include the use of the one additional agent that inhibits hepatic virus infection to NPC1L1 antagonist at a ratio of 1 to 20-200, or more desirably 1 to 30-100.

For use in the methods of the invention, desirably the synergistic composition is formulated for administration to a subject. In this respect, the NPC1L1 antagonist and at least one additional agent that inhibits hepatic virus infection can be combined in appropriate amounts in admixture with one or more pharmaceutically acceptable carriers. Such carriers are well-known in the art and include, e.g., saline solution, cellulose, lactose, sucrose, mannitol, sorbitol, and calcium phosphates. Optional additives include lubricants and flow conditioners, e.g., silicic acid, silicon dioxide, talc, stearic acid, magnesium/calcium stearates and polyethylene glycol (PEG) diluents; disintegrating agents, e.g., starch, carboxymethyl starch, cross-linked PVP, agar, alginic acid and alginates, coloring agents, flavoring agents and melting agents. Dyes or pigments may be added to tablets or dragee coatings, for example, for identification purposes or to indicate different doses of active ingredient.

Generally, the active ingredients are present in an amount of 1-95% by weight of the total weight of the synergistic composition. The composition may be provided in a dosage form that is suitable for the oral, parenteral (e.g., intravenously or intramuscularly), rectal, determatological, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, injectables, implants, sprays, or aerosols. The pharmaceutical compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, N.Y.).

It is contemplated that the NPC1L1 antagonist and at least one additional agent that inhibits hepatic virus infection can be formulated in a single formulation or multiple formulations with simultaneous or consecutive (e.g., within minutes, days or hours) administration.

The dosage of a compound or a combination of compounds depends on several factors, including the administration method, the type of viral hepatitis to be treated, the severity of the infection, whether dosage is designed to treat or prevent a viral hepatitis infection, and the age, weight, and health of the patient to be treated.

Because the synergistic composition of the invention targets both viral entry/cell-to-cell spread and gene expression, replication, assembly, maturation and/or egress, this composition finds use in methods for effecting clearance of a hepatic virus from a cell and treating a hepatic virus infection.

Accordingly, the present invention also embraces a method for effecting clearance of a hepatic virus from a cell. This method involves contacting a hepatic virus-infected cell with an effective amount of the synergistic composition of the invention so that the hepatic virus is cleared from the cell. Desirably, the synergistic composition provides at least a 20%, 30%, 50%, 70%, 80%, 90%, 95%, or 99% decrease in viral load from the cell, as determined using a suitable assay. According to particular embodiments of this invention, a cell of this method is a hepatic cell. By affecting clearance of a hepatic virus from a cell, this method of the invention finds use in the treatment of a hepatic virus infection.

Accordingly, another embodiment of the present invention embraces a method for treating a hepatic virus infection by administering to a subject with a hepatic virus infection an effective amount of the synergistic composition of the invention so that the hepatic virus infection is treated. In the context of the present invention, "treat" or "treating" refers to the administration of a synergistic composition to measurably slow or stop viral replication or spread, to measurably decrease the load of a virus (e.g., any virus described herein including a hepatitis virus such as hepatitis A, B, C, D, or E), and/or to reduce at least one symptom associated with a hepatic virus infection. Desirably, the slowing in replication or the decrease in viral load is at least 20%, 30%, 50%, 70%, 80%, 90%, 95%, or 99%, as determined using a suitable assay (e.g., a replication assay or infection assay described herein).

Subjects benefiting from treatment include those diagnosed with a hepatic virus infection, e.g., an individual in which a hepatic virus marker has been detected. A variety of markers are known in the art and can be readily measured by a skilled artisan. For example, HCV infection can be diagnosed by the presence of the viral genome or proteins in the liver or blood.

In the context of prophylactic and therapeutic use, "an effective amount" of a composition herein is defined as an amount of an agent which reduces or eliminates viral load to reduce, mitigate or eliminate chronic infection, which leads to cancer or cirrhosis (with symptoms such as enlarged liver, enlarged spleen, jaundice, muscle wasting excoriations, ascites and ankle swelling).

An effective amount for use in accordance with the present methods can be determined by a variety of means well known to those of skill in the art. For example, it is contemplated that one of skill in the art can choose an effective amount using an appropriate animal model system, e.g., as described herein, to test for inhibition of HCV in vivo. The medical literature provides detailed disclosure on the advantages and uses of a wide variety of such models. Once a test drug has shown to be effective in vivo in animals, clinical studies can be designed based on the doses shown to be safe and effective in animals. One of skill in the art can design such clinical studies using standard protocols as described in textbooks such as Spilker ((2000) *Guide to Clinical Trials*. Lippincott Williams & Wilkins: Pa.).

In the present invention, doses of drugs to be administered in the methods of the present invention can be chosen by one of skill in the art based on the known pharmacology and toxicology of ezetimibe, or its derivatives, and interferon or other inhibitors as they are used in clinical medicine. One of skill would choose doses using resources such as the currently approved product labeling for these drugs. It is contemplated that these doses would be individualized for a patient based on the judgment of the physician.

If desired, the compounds of the invention may be employed in mechanistic assays to determine whether other combinations, or single agents, are as effective as the combinations of the invention in inhibiting a viral disease using assays generally known in the art. For example, candidate compounds can be tested, alone or in combination (e.g., with a NPC1L1 antagonist) and applied to cells (e.g., hepatic cells such as Huh7, Huh2, Huh 8, Sk-Hep-1, Huh7 lunet, HepG2, WRL-68, FCA-1, LX-1, LX-2, Huh7-derived cells lines). After a suitable time, viral entry and replication or load of these cells is examined. A decrease in viral entry (e.g., as determined by a standard foci formation assay), replication or viral load identifies a candidate compound or combination of agents as an effective agent for treating a viral disease.

The compounds disclosed herein are also useful tools in elucidating mechanistic information about the biological pathways involved in viral diseases. Such information can lead to the development of new combinations or single agents for treating, preventing, or reducing a viral disease. Methods known in the art to determine biological pathways can be used to determine the pathway, or network of pathways affected by contacting cells (e.g., hepatic cells) infected with a virus with the compounds of the invention. Such methods can include, analyzing cellular constituents that are expressed or repressed after contact with the compounds of the invention as compared to untreated, positive or negative control compounds, and/or new single agents and combinations, or analyzing some other activity of the cell or virus such as an enzymatic activity, nutrient uptake, and proliferation. Cellular components analyzed can include gene transcripts, and protein expression. Suitable methods can include standard biochemistry techniques, radiolabeling the compounds of the invention, and observing the compounds binding to proteins, e.g., using 2D gels and/or gene expression profiling. Once identified, such compounds can be used in in vivo models (e.g., knockout or transgenic mice) to further validate the tool or develop new agents or strategies to treat viral disease.

The invention is described in greater detail by the following non-limiting examples.

Example 1

Methods

Cells.

Huh7 cells, also known as Huh7/scr cells, are well-known in the art (Zhong, et al. (2005) *Proc. Natl. Acad. Sci. USA* 102, 9294-99; Gastaminza, et al. (2006) *J. Virol.* 80:11074-81; Zhong, et al. (2006) *J. Virol.* 80:11082-93; Sainz et al. (2009) *PLoS ONE* 4:e6561). The Clone B HCV genotype 1b subgenomic replicon (sg1b) Huh7 cells were obtained through the NIH AIDS Research and Reference Reagent Program and have been previously described (Blight, et al. (2000) *Science* 290:1972-1974). The HCV sg2a replicon was established as previously described (Uprichard, et al. (2006) *Virol. J.* 3:89). Briefly the HCV genotype 2a subgenomic replicon RNA (psgJFH1; Kato, et al. (2003) *Gastroenterology* 125:1808-17) was XbaI linearized, in vitro transcribed using MEGASCRIPT T7 (Ambion, Austin, Tex.) and transfected into cells using a modified electroporation protocol (Krieger, et al. (2001) *J. Virol.* 75(10):4614-24). All cells were cultured in complete Dulbecco's modified Eagle's medium (cDMEM) (Hyclone, Logan, Utah) supplemented with 10% fetal bovine serum (FBS) (Hyclone), 100 units/ml penicillin, 100 mg/ml streptomycin, and 2 mM L-glutamine (Gibco Invitrogen, Carlsbad, Calif.) and 500 µg/ml geneticin ((Invitrogen) for HCV replicon cells only).

HCVcc Generation.

The plasmid containing the full-length JFH-1 genome (pJFH1) has been previously described (Kato, et al. (2003)

supra; Kato, et al. (2001) *J. Med. Virol.* 64:334-9; Wakita, et al. (2005) *Nat. Med.* 11:791-6). Protocols for JFH-1 in vitro transcription and HCV RNA electroporation have been described (Uprichard, et al. (2006) supra). The JFH-1 HCVcc viral stock was generated by infection of naïve Huh7 cells at a multiplicity of infection (MOI) of 0.01 focus forming units (FFU)/cell using medium collected of day 18 post-electroporation of Huh7 cells with in vitro transcribed JFH-1 RNA (Zhong, et al. (2005) supra).

Reagents.

Recombinant human interferon-α 2a (IFN-α2a) and IFN-β (PBL Biomedical Laboratories, New Brunswick, N.J.) were resuspended to a concentration of 50 U/µl in complete DMEM supplemented with 10% FBS, aliquoted into single use tubes, and stored at −80° C. Ezetimibe was resuspended to a concentration of 20 mM in DMSO and stored at 4° C. The protease inhibitor, ITMN 5537 (Intermune, Brisbane, Calif.) was resuspended to 10 mM in DMSO.

Treatment of Acute HCVcc Infections.

For experiments in growing cells, Huh7 cells were seeded 24 hours prior to use at $4\times10^3$ cells in each well of a 96-well plate (BD Biosciences, San Jose, Calif.). For experiments in non-growing cells, Huh7 cells were seeded in 96-well BIO-COAT culture plates (BD Biosciences) at a density of $8\times10^3$ cells/well in cDMEM. Upon reaching 90% confluence, media was replaced with 200 µl cDMEM supplemented with 1% (v/v) DMSO (Sigma), and cells were cultured for an additional 20 days, replacing medium every 2 days (Sainz, Jr. & Chisari (2006) *J. Virol.* 80:10253-7; Choi, et al. (2009) *Xenobiotica* 39:205-17). Cells were infected with HCVcc JFH-1 at an MOI of 1.0 or 0.1 FFU/cell for 12 hours. Cells were mock-treated or treated with increasing concentrations of ezetimibe 6 hours prior to infection (PRE), during the time of infection for 12 hours (CO), or immediately following infection for 60 hours (POST). For RT-qPCR analysis, total cellular RNA was extracted in 1× Nucleic Acid Purification Lysis Solution (Applied Biosystems, Foster City, Calif.) from triplicate wells at indicated times post infection. For HCV E2-positive foci assay analysis, medium was removed and cells were fixed with 4% paraformaldehyde (w/v) (Sigma) 72 hours post-infection and immunohistochemical staining for HCV E2 was performed as described herein.

Treatment of Chronic HCVcc Infections.

For experiments in growing cells, Huh7 cells seeded at $1\times10^6$ cells in a T75 cell culture flask (Corning) were infected with JFH-1 HCVcc at a MOI of 0.01 FFU/cell and subsequently cultured for 10 days to allow HCV RNA to reach steady-state levels. On day 10 post-infection, cells were split 1:4 and re-plated into T25 culture flasks (Corning). Twenty four hours post seeding, individual flasks were mock-treated with cDMEM or treated with cDMEM containing IFN-α (100 U/ml), ezetimibe (30 µM) or a combination of both IFN-α (100 U/ml) and ezetimibe (30 µM). Throughout the course of the experiment, fresh media with treatments was replenished every two days and cells were trypsinized just before reaching confluence and re-plated at a dilution of 1:3 to maintain active cell growth. Samples were collected at the time of each splitting, excess cells were pelleted at 1200 rotations per minute for 5 minutes and total RNA was isolated in 1× Nucleic Acid Purification Lysis Solution (Applied Biosystems) for reverse transcription followed by RT-qPCR analysis.

For experiments in non-growing cells, Huh7 cells were seeded in 48-well BIOCOAT culture plates (BD Biosciences) at a density of $1\times10^4$ cells/well and subsequently cultured in the presence of 1% DMSO for 20 days as described herein. Cultures were infected with JFH-1 HCVcc at a MOI of 0.01 FFU/cell and maintained for 14 days to allow HCV RNA to reach steady-state levels. On day 14 post-infection, wells were mock-treated with cDMEM or treated with DMEM containing IFN-α, ezetimibe or a combination of both, as described herein for growing Huh7 cultures. Media and respective treatments were replenished every 2 days. On indicated days post-treatment, total RNA was isolated from triplicate wells in 1× Nucleic Acid Purification Lysis Solution (Applied Biosystems) for reverse transcription followed by RT-qPCR analysis.

For experiments analyzing the activity of ezetimibe in combination with a protease inhibitor, Huh7-1 cells were infected with HCV-JFH-1 and allowed to reach steady state levels of infection. The HCV-infected cells were seeded in a 96-well plate and treated with the following: medium alone, 30 µM ezetimibe, 200 nM ITMN5537, 100 µ/ml IFN-α, and combinations of the above drugs at the specified concentrations. Medium and drugs were replaced every 24 hours. Triplicate wells were harvested at 24, 48, 72 or 96 hours post-treatment, in 200 µl/well of 1×ABI lysis buffer and stored at −80° C. until RNA extraction.

RNA Isolation and RT-qPCR Analysis.

Total cellular RNA was purified using an ABI PRISM™ 6100 Nucleic Acid PrepStation (Applied Biosystems), as per the manufacturer's instructions. One µg of purified RNA was used for cDNA synthesis using the TAQMAN reverse transcription reagents (Applied Biosystems), followed by SYBR green RT-qPCR using an Applied Biosystems 7300 real-time thermocycler (Applied Biosystems). Thermal cycling included of an initial 10-minute denaturation step at 95° C. followed by 40 cycles of denaturation (15 seconds at 95° C.) and annealing/extension (1 minute at 60° C.). HCV JFH-1 and human GAPDH RNA transcript levels were determined relative to a standard curve derived from serial dilutions of plasmid containing the JFH-1 HCV cDNA or the human GAPDH coding sequence, respectively. The PCR primers used to amplify each amplicon were: human GAPDH (NMX002046) 5'-GAA GGT GAA GGT CGG AGT C-3' (sense; SEQ ID NO:1) and 5'-GAA GAT GGT GAT GGG ATT TC-3' (anti-sense; SEQ ID NO:2); and JFH-1 HCV (AB047639) 5'-TCT GCG GAA CCG GTG AGT A-3' (sense; SEQ ID NO:3)) and 5'-TCA GGC AGT ACC ACA AGG C-3' (anti-sense; SEQ ID NO:4) or universal HCV primers (Komurian-Pradel, et al. (2004) *J. Virol. Methods* 116(1):103-6) 5'-GCC TAG CCA TGG CGT TAG TA-3' (sense; SEQ ID NO:5) and 5'-CTC CCG GGG CACTCG CAA GC-3' (anti-sense; SEQ ID NO:6).

Extracellular Infectivity Titration Assay.

Cell supernatants were serially diluted 10-fold in cDMEM and 100 µl was used to infect, in triplicate, $4\times10^3$ naïve Huh7 cells per well in 96-well plates (BD Biosciences). The inoculum was incubated with cells for 24 hours at 37° C. and then overlayed with 150 µl complete DMEM containing 0.4% methylcellulose (w/v) (Fluka BioChemika, Switzerland) to give a final concentration of 0.25% methylcellulose. Seventy-two hours post-infection, medium was removed, cells were fixed with 4% paraformaldehyde (Sigma) and immunohistochemical staining for HCV E2 was performed. Briefly, cells were first incubated with 1×PBS containing 0.3% (v/v) hydrogen peroxide (Fisher, Fairlawn, N.J.) to block endogenous peroxidase. Following three rinses with 1× PBS, cells were blocked for 1 hour with 1×PBS containing 0.5% (v/v) TRITON X-100 (Fisher), 3% (w/v) bovine serum albumin (BSA) (Sigma) and 10% (v/v) FBS. The HCV E2 glycoprotein was detected by incubation at room temperature with 1×PBS containing 0.5% (v/v) TRITON X-100 and 3% (w/v) BSA and a 1:500 dilution of the human monoclonal anti- HCV E2 antibody C1. Bound C1 was subsequently detected by a 1 hour incubation with a 1:1000 dilution of an HRP-conjugated anti-human antibody (Pierce, Rockford, Ill.) followed by a 30 minute incubation with an AEC detection substrate (BD Biosciences). Cells were washed with distilled $H_2O$ and visualized using a ZEISS AXIOVERT microscope (Carl Zeiss, Germany). Viral infectivity titers are expressed as FFU per milliliter of supernatant (FFU/ml), determined by the average number of E2-positive foci detected in triplicate samples at the highest HCV-positive dilution.

Western Blot Analysis.

Cells were harvested in 1.25% TRITON X-100 lysis buffer (TRITON X-100, 50 mM Tris-HCl, pH 7.5, 150 mM NaCl, 2 mM EDTA) supplemented with a protease inhibitor cocktail (Roche Applied Science, Indianapolis). Fifty micrograms of protein was resolved by SDS-PAGE and transferred to HYBOND nitrocellulose membranes (Amersham Pharmacia, Piscataway, N.J.). Membranes were sequentially blocked with 5% Nonfat Milk, incubated with a 1:1000 dilution of a monoclonal mouse anti-HCV NS3 antibody (Clone 9-G2, ViroGen, Watertown, Mass.), washed 3 times with PBS/0.05% TWEEN 20, incubated with horseradish peroxidase-conjugated goat anti-mouse antibody (Pierce, Rockford, Ill.), and washed again. Bound antibody complexes were detected with SUPERSIGNAL chemiluminescent substrate (Pierce).

Cell Proliferation and Cytotoxicity Bioluminescence Assays.

The VIALIGHT Plus Cell Proliferation assay kit (Lonza, Walkersville, Md.), which incorporates bioluminescent detection of cellular ATP as a measure of cell viability and proliferation, was used according to the manufacturer's instructions. Briefly, mock-treated and drug-treated cultures were lysed in Cell Lysis reagent for minutes. One hundred µl of culture medium was transferred to white 96-well plates (BD Biosciences) containing ATP detection reagent and luminescence, expressed as relative light units (RLU), was measured (Fluostar OPTIMA). To assess drug-induced cellular toxicity, a bioluminescence-based assay (The TOXILIGHT BioAssay Kit, Lonza) that measures adenylate kinase (AK) released from damaged cells was used as per the manufacturer's instructions. Briefly, 20 µl of supernatant was collected on indicated days and transferred to white 96-well plates (BD Biosciences). One hundred µl of AK detection reagent was then added to each well, and luminescence (RLU) was measured (Fluostar OPTIMA). In general, cytotoxicity analysis demonstrated that ezetimibe treatment of Huh7 cells for 12 hours was not cytotoxic at the concentrations tested.

Statistics.

Data are presented as the means standard error of the means (sem). Significant differences were determined by one-way analysis of variance (ANOVA) followed by Tukey's post hoc t test (GRAPHPAD PRISM Software, San Diego, Calif.).

Example 2

Ezetimibe Blocks Entry of HCV Into Cells

Ezetimibe, a 2-azetidinone class of drug, is an anti-hyperlipidemic, cholesterol-lowering medication which has been shown to inhibit cholesterol absorption in vivo, lowering plasma LDL and total cholesterol in treated individuals (Gupta & Ito (2002) *Heart Dis.* 4:399-409; Bays, et al. (2008) *Expert Rev. Cardiovasc. Ther.* 6:447-70). Since infectious HCV particles are enriched in cellular cholesterol (Aizaki, et al. (2008) *J. Virol.* 82:5715-24), it was contemplated that ezetimibe might also inhibit HCV entry into cells. As such, the ability of ezetimibe to inhibit HCV entry was evaluated by performing a HCV foci reduction assay. Huh7 cells were inoculated with cell culture-produced HCV (HCVcc) at a multiplicity of infection (MOI) of 1.0 or 0.1 focus forming units (FFU)/cell and treated with increasing concentrations (0, 3.125, 6.25, 12.5 and 25 µM) of ezetimibe pre-, co- or post-infection. Ezetimibe reduced HCV foci formation in a dose-dependent manner relative to untreated cells (0 µM ezetimibe) when present for 6 hours prior to infection and then removed or during the 12 hour virus inoculation period and then removed. Specifically, pre-treatment of cells with 12.5 or 25 µM ezetimibe, inhibited HCV foci formation by 85 and 95%, respectively, compared to untreated cultures, while more potent inhibition of 90 and 99% was observed when cells were co-incubated with HCVcc and ezetimibe at 12.5 µM or 25 µM, respectively. However, the degree of inhibition observed was greatly reduced when ezetimibe was added to cells post-infection (p.i.).

Likewise dose-dependent and time-of-addition-dependent inhibition of HCV infection was observed when HCV RNA levels were quantified by RT-qPCR 24, 48 and 72 hours p.i. Notably, pre-treatment with 25 µM ezetimibe for 6 hours before infection appeared to protect cells from subsequent infection for at least 48 hours. Co-treatment also potently inhibited HCV infection, but again consistent with the effects of an entry inhibitor, addition of ezetimibe post-infection was ineffective with only marginal reduction in HCV RNA levels detected at 72 hours p.i.

To ensure that the inhibition observed was not due to ezetimibe-induced changes in cell proliferation or cytotoxicity, cellular ATP was measured as a read-out of Huh7 cell viability and proliferation and cellular toxicity by adenylate kinase release following treatment with increasing doses of ezetimibe. These results confirmed that ezetimibe treatment did not inhibit cell proliferation or induce cellular toxicity at any of the doses used. Furthermore, similar ezetimibe-mediated inhibition was obtained in analogous experiments performed using non-growing Huh7 cell cultures (Saint, Jr. & Chisari (2006) *J. Virol.* 80:10253-7), which better mimic the non-dividing state of hepatocytes in vivo. Furthermore, to test the specificity of the observed HCV inhibition, the effect of ezetimibe on entry of another flavivirus, Dengue virus (DNV), was assessed. Unlike HCV, no significant reduction in DNV plaque formation was observed upon treating cells with 12.5 or 25 µM ezetimibe. Thus taken together, these data indicate that ezetimibe is a potent and specific inhibitor of an early step in HCVcc infection.

To confirm that ezetimibe does not inhibit HCV RNA replication, as has been shown for other anti-hyperlipidemic cholesterol-lowering medications that target the cholesterol biosynthetic pathway rather than uptake of free cholesterol, the effect of ezetimibe on HCV replication was directly assayed by treating Huh7 cells constitutively replicating HCV genotype 2a or 1b subgenomic (sg) replicons with increasing doses of ezetimibe. As a positive control, cells were also treated in parallel treatment with Lovastatin, an inhibitor of the cholesterol biosynthetic pathway that has been shown to reduce HCV sg1b RNA replication (Kapadia & Chisari (2005) *Proc. Natl. Acad. Sci. USA* 102:2561-6; Ye, et al. (2003) *Proc. Natl. Acad. Sci. USA* 100:15865-70; Tobert (2003) *Nat. Rev. Drug Discov.* 2:517-26) and HCVcc particle secretion (Kapadia & Chisari (2005) supra). Consistent with previous reports, Lovastatin reduced sg1b RNA levels 22-fold by 72 hours post-treatment, as determined by RT-qPCR analysis, but had no affect on sg2a RNA levels. In contrast, no significant reduction of sg1b or sg2a HCV RNA steady-state levels was observed in the presence of increasing doses of ezetimibe. Similar results were obtained at 24 and 48 hours post-treatment. Additionally, when evaluated as an inhibitor of HCVcc foci formation, Lovastatin had no affect when added pre-, co- or post-infection. Thus, together, these results show that while inhibitors of cholesterol biosynthesis, such as Lovastatin, inhibit HCV RNA replication and particle egress, unlike ezetimibe they do not affect HCV entry.

Figure 1:
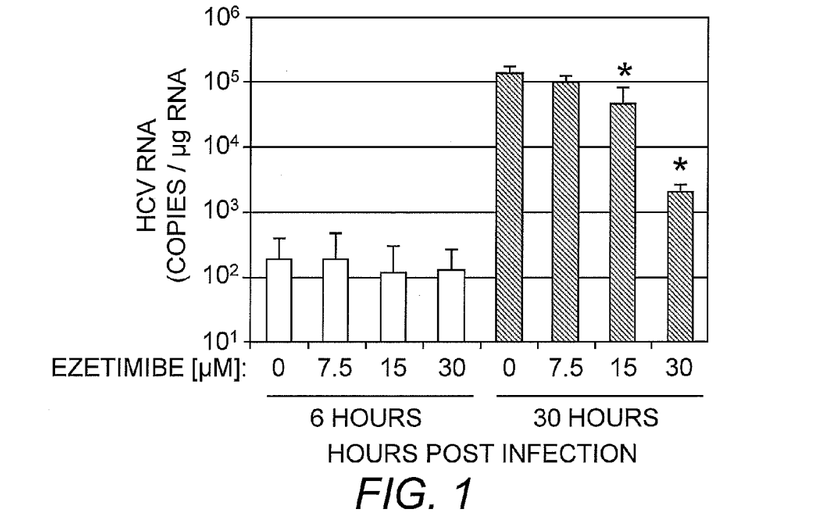

To decipher whether ezetimibe inhibits HCV cellular binding or subsequent internalization, cell-associated HCV RNA and protein in mock- and ezetimibe-treated HCVcc-infected cultures was examined. Consistent with ezetimibe not inhibiting virion binding, similar levels of HCV RNA were detected in inoculated cells 6 hours p.i, in the absence or presence of ezetimibe (FIG. 1). In contrast, HCV entry, indicated by HCV RNA expansion and de novo NS5A protein expression was not observed at later time points in ezetimibe-treated cultures, indicating that although HCV can efficiently bind to ezetimibe-treated Huh7 cells, a post-binding step required for infection initiation was prevented.

Figure 2A:
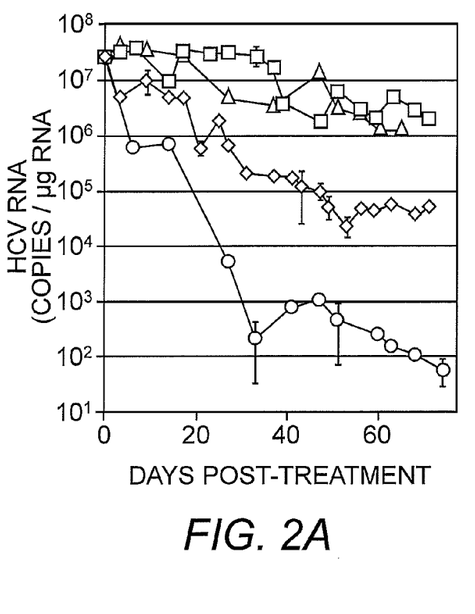
FIG. 2 shows that ezetimibe synergizes with IFN-α to potently inhibit HCV RNA levels in chronically infected Huh7 cells. Cultures of growing Huh7 cells were inoculated with HCVcc JFH-1 at an MOT of 0.01 FFU/cell. Infected cultures were maintained for an additional 10 days to allow HCV RNA to reach steady-state levels.

Importantly, because IFN-α has been the foundation of chronic HCV treatment since the 1980's, experiments examining the combined effect of interferon with ezetimibe were performed on chronically-infected Huh7 cultures. Specifically, Huh7 cells were infected with HCVcc and cultured for 14 days to allow HCV RNA to reach steady-state levels. Parallel cultures were then mock-treated or treated with ezetimibe, IFN-α or a combination of both while being maintained in an actively growing state for ~70 days by splitting cultures 1:3 upon reaching 90% confluence. Consistent with an entry inhibitor, addition of ezetimibe alone did not reduce intracellular HCV steady-state RNA levels throughout the course of treatment, while IFN-α (100 U/ml) alone decreased intracellular HCV RNA levels by ~2 logs by day 32 post-treatment compared to the mock-treated culture. Notably, when IFN-α was used in combination with 15 μM or 30 μM ezetimibe (FIG. 2A), a strong synergistic affect was observed. IFN-α in combination with 30 μM ezetimibe potently reduced HCV RNA to background levels (≥5 logs decrease) by 32 days post-treatment, indicating that the chronically-infected culture had been cured.

Figure 2B:
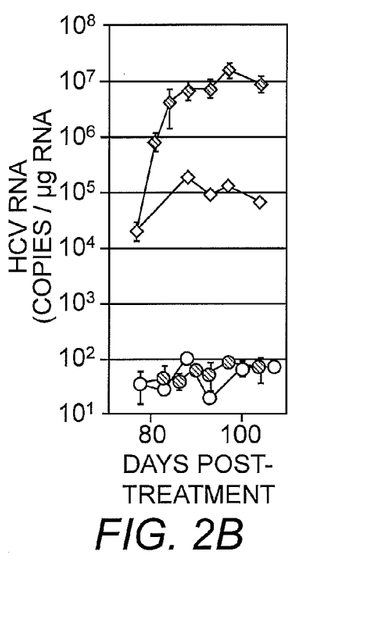

To confirm HCV clearance, drug treatments were subsequently discontinued on day 70 and HCV RNA levels were monitored for an additional 30 days. While an immediate rebound in HCV RNA to levels equivalent to those measured in non-treated control cultures was observed in cultures that had been previously maintained in the presence of 100 U/ml IFN-α (FIG. 2B), no rebound in HCV RNA (FIG. 2B) or evidence of HCV proteins by immunohistochemical staining was observed in cultures that had been previously maintained in the presence of combination treatment with IFN-α (100 U/ml) and ezetimibe (30 μM). IFN-α also acted synergistically with ezetimibe in non-growing chronically infected Huh7 cell cultures resulting in over a log greater reduction in HCV RNA by day 56 post treatment compared to IFN-α treatment alone.

Similar studies were carried out with IFN-β alone (20 U/ml), or ezetimibe and IFN-β in combination (a combination of either 15 or 30 μM ezetimibe with 20 U/ml IFN-β). Intracellular RNA was collected from triplicate wells weekly for 8 weeks post-treatment and HCV RNA was quantified by RT-qPCR. Ezetimibe treatment alone did not reduce HCV infection (i.e., steady-state intracellular HCV RNA levels) during the experiment. IFN-β treatment alone significantly reduced intracellular HCV RNA levels (approximately 100-fold) from week 3 to week 8 as compared to mock treated (controls), indicating pharmacological activity to inhibit chronic HCV infection. Importantly, however, a synergistic effect was observed when IFN-β was used in combination with ezetimibe at concentrations of 15 or 30 μM. Specifically, IFN-β (20 U/ml) in combination with 30 μM ezetimibe synergistically reduced HCV RNA levels by >10,000-fold by week 4 post treatment and by >50,000-fold by week 6 to week 8 post treatment, as compared to mock treated HCV cultures (controls). The level of HCV RNA copies measured were equivalent to background levels, indicating that the cultures had been "cured" of HCV. It was confirmed that the inhibition observed was not a consequence of treatment-induced cytotoxicity.

Together, these data demonstrate that regardless of the degree of host hepatocyte proliferation, ezetimibe functions in synergy with both IFN-α and IFN-β to potently reduce chronic HCV infection in vitro. Therefore, whether alone or as an adjunct therapy to current HCV interferon therapy protocols, ezetimibe finds application in the prevention or treatment of HCV infection.

Example 3

Role of NPC1L1 in HCV Entry

Studies have shown that a G451R mutation in the viral envelope glycoprotein (E2) results in HCV virions of higher density and faster infection kinetics (thong, et al. (2006) *J. Virol.* 80:11082-11093). In addition it has been determined that this mutant displays a reduced dependence on SR-B1 for cellular entry (Grove, et al. (2008) *J. Virol.* 82:12020-12029). Thus, if ezetimibe was blocking HCV entry via an SR-B1 mediated mechanism, it would be expected that the mutant G451R virus would be less susceptible to the effects of ezetimibe. As a result, experiments were performed to assess the antiviral efficacy of ezetimibe against the SR-B1-independent HCVcc$^{G451R}$ virus. Monolayers of Huh7 cells were inoculated with either wild-type HCVcc$^{JFH-1}$ or HCVcc$^{G451R}$ at an MOI of 0.01 FFU/cell for 12 hours. Ezetimibe treatment at concentrations of 15 or 30 μM was initiated (and then continued) either 6 hours prior to infection, during the 12 hour incubation of the virus on the cells, or immediately following the 12 hour viral inoculation period. Ezetimibe at a concentration of 30 μM inhibited HCVcc$^{JFH-1}$ infection approximately 10-fold at 48 hours post-infection. The HCVcc$^{G451R}$ virus was significantly more sensitive to the inhibitory effects of ezetimibe with virtually 100% of the infection being blocked by ezetimibe, as indicated by the lack of significant intracellular HCV RNA following infection. These data indicate that the inhibitory effect of ezetimibe on HCV entry is not mediated by SR-B1.

Therefore, it was determined whether the Neiman-Pick C1 Like-1 cholesterol uptake receptor (Ge, et al. (2008) *Cell Metab.* 7:508-19; Chang & Chang (2008) *Cell Metab.* 7:469-71; Weinglass, et al. (2008) *Proc. Natl. Acad. Sci. USA* 105:11140-5) plays a direct role as a HCV entry receptor.

NPCIL1 Silencing Inhibits HCVcc Infectivity.

To more directly confirm that NPC1L1 is an HCVcc entry factor, it was determined whether silencing of human NPC1L1 by RNA interference (RNAi) would reduce HCVcc infection in Huh7 cells. In addition, a siRNA specific for the known HCV receptor, scavenger receptor class B member I (SR-BI), was included as a positive control. Huh7 cells were transfected with either control siRNAs or siRNAs specific for human NPC1L1 or SR-B1 and knockdown was confirmed by RT-qPCR. Cells with NCPIL1 or SR-B1 knockdown were subsequently infected with HCVcc 48 hours post-transfection. Consistent with being HCV entry factors, both SR-B1 and NPC1L1 knockdown significantly reduced HCVcc infectivity (>90%) independently confirming that NPC1L1 is necessary for HCVcc infection.

HCVcc Binds to NPC1L1 Expressing CHO Cells.

To determine if HCVcc particles bind NPC1L1 in the absence of the other HCV receptors, Chinese Hamster Ovary Cells (CHO cells) were transiently transfected with an NPC1L1 expression vector (pCDNA3.1-huNPC1L1-HA) and incubated with HCVcc for 6 hours. Following rigorous washing, bound virus was measured by RT-qPCR analysis. The results of this analysis indicated that CHO cells expressing SR-B1 but not CD81 bound HCVcc. Notably, similar to CHO cells expressing SR-B1, CHO cells expressing only NPC1L1 bound 3 times more HCVcc than CHO expressing a GFP or empty vector control plasmid. Together, these data indicate that NPC1L1 is an HCV entry factor and that HCVcc directly interacts with this receptor. As such, the data also indicate that other compounds that block NPC1L1 are also useful as inhibitors of HCV entry.

Example 4

In Vivo Activity of Ezetimibe

Studies of HCV infection and agents that can be used to prevent or treat infection have been hampered by the lack of small animal models of HCV infection. Although efforts to develop small animal infection models have included use of tree shrews (Xie, et al. (1998) *Virology* 244:513-520; Zhao, et al. (2002) *J. Clin. Invest.* 109:221-232), marmosets/tamarins (Feinstone, et al. (1982) *J. Infect. Dis.* 144:588-598; Karayiannis, et al. (1983) *J. Med. Virol.* 11:251-256; Watanabe, et al. (1987) *J. Med. Virol.* 22:143-156), and other primates (Abe, et al. (1993) *J. Med. Primatol.* 22:433-434), successful transmission of HCV infection has only been observed in the chimpanzee. Recently, hepatic xenorepopulation approaches have become an art acceptable means of creating murine models of HCV infection (Knetman & Mercer (2005) *Hepatology* 41:703-706; Kneteman & Toso (2009) *Methods Mol. Biol.* 510:383-399; Grompe, et al. (1999) *Semin. Liv. Dis.* 19:7-14). This approach involves transplanting primary human hepatocytes into immunodeficient mice which have a lethal defect in their own endogenous hepatocytes. As the endogenous mouse hepatocytes die, transplanted primary human hepatocytes can repopulate the mouse liver, resulting in mice with chimeric human livers permissive for HCV infection.

Therefore, to demonstrate in vivo activity of ezetimibe, experiments are performed using mice triply mutant for Fah, Rag2 and the common γ-chain of the interleukin receptor (Fah$^{-/-}$/Rag2$^{-/-}$/Il2rg$^{-/-}$ mice), which have been shown to be readily permissive for hepatic xenorepopulation (Azuma, et al. (2007) *Nat. Biotechnol.* 25:903-910; Schultz, et al. (2007) *Nat. Rev. Immunol.* 7:118-130). Alternatively, severe combined immunodeficient (SCID)/urokinase plasminogen activator (uPA) mice can be used. Mice are transplanted with primary human hepatocytes according to conventional methods (Azuma, et al. (2007) *Nat. Biotechnol.* 25:903-910; Bissig, et al. (2007) *Proc. Natl. Acad. Sci. USA* 104:20507-20511) and monitored for two months post-transplantation to assess repopulation efficiency by measuring human albumin serum levels. Using these models, mice can be assessed for the prevention of HCV infection or the inhibition of an already established infection.

To demonstrate prevention, mice are treated with either 1) ezetimibe at a dose of 10 mg/kg/day via oral gavage or 2) a diluent control via oral gavage approximately 7 days prior to infection with HCV. Mice are injected with HCV positive human serum (of any HCV genotype) and HCV RNA serum levels are quantified daily and/or weekly to assess the efficacy with which the treatments reduces the amplification of HCV RNA levels. Evidence that ezetimibe reduces the amplification HCV levels in vivo, as compared to untreated animals, provides in vivo evidence that ezetimibe is an effective treatment for HCV in patients. In this respect, it is expected that ezetimibe prevents the establishment of HCV infection.

To demonstrate treatment, mice are infected with HCV positive human serum (of any HCV genotype). HCV RNA serum levels are assessed routinely to confirm infection and monitor the establishment of a steady-state chronic infection in vivo. Groups of chronically HCV-infected chimeric mice are then treated in parallel with either (1) a type I interferon (e.g., PEGASYS at 30 μg/kg twice weekly via subcutaneous injection), (2) ezetimibe alone at a dose of 10 mg/kg/day via oral gavage, or (3) a combination of both type I interferon (e.g., PEGASYS at 30 μg/kg twice weekly) and ezetimibe (10 mg/kg/day). During the treatment period, HCV RNA serum levels are quantified weekly to assess the efficacy with which the treatments reduce steady-state HCV RNA levels. Evidence that ezetimibe alone or in combination with IFN reduces HCV levels in vivo, provides in vivo evidence that ezetimibe is an effective treatment for HCV in patients. In this respect, it is expected that ezetimibe in combination with a type I interferon will synergistically enhance clearance of HCV infection when compared to type I interferon or ezetimibe alone.

Example 5

Clinical Analysis of Ezetimibe

Studies have indicated that interferon and ribavirin work by blocking HCV production and upregulating the host immune response to produce clearance of infected hepatocytes (Neumann, et al. (1998) *Science* 282:103-107). Small molecules are in development, which target the HCV NS3 protease and the viral polymerase in an effort to further improve the efficacy of antiviral therapy. However, to date, no FDA-approved treatment has been shown to block uptake of HCV into uninfected liver cells. An agent that inhibits de novo infection of hepatocytes would not only prevent initial spread of the virus in the liver, but also be complementary to the available medications and could have a dramatic impact on sustained Virologic Response (SVR) rates (i.e., viral clearance) and serve to prevent or slow infection of the new liver post-transplantation.

To compare safety and efficacy of the combination ezetimibe, interferon, and ribavirin with the standard of care derived from interferon and ribavirin for the treatment of hepatitis C infection in humans, clinical studies are carried out. Subjects selected for the trial are patients who are due to receive routine treatment for HCV with interferon plus ribavirin. Using a prospective randomized study design with two arms, patients are randomized 1:1 to treatment with ezetimibe vs. no ezetimibe. All patients receive interferon plus ribavirin per a typical protocol. Group 1 receives ezetimibe, 10 mg per day, for 14 days prior to interferon and ribavirin to assess tolerability and to assess impact of ezetimibe monotherapy on HCV RNA level. Participants are then given ezetimibe, 10 mg per day, during the first three months of interferon and ribavirin therapy. Group 2 receives only the standard of care for treatment of HCV, i.e., interferon and ribavirin.

All subjects have the normal routine laboratory monitoring performed for patients receiving treatment for hepatitis C.

Specifically, baseline HCV RNA level and genotype are assessed and HCV RNA levels are measured at week 4, 12, 24, end of treatment, and 24 weeks post-treatment. In addition, for the purposes of the study, HCV RNA levels are assessed on day −14, 0, 2, 7, and 14. The primary study endpoint for assessment of efficacy of drug treatment is the difference in serum HCV RNA decrease as well as proportion of patients with undetectable HCV RNA at week 4 of antiviral therapy. Specifically, the degree of serum HCV RNA decrease in Group 1 is compared to Group 2 to assess whether the addition of ezetimibe to the standard of care enhances HCV inhibition and in particular whether the addition of ezetimibe to the standard of care increases the HCV clearance rate. The secondary endpoint is the slope of HCV RNA decline over the first two weeks in Group 1 versus Group 2, as this has proven to be an early predictor of SVR.

Similar clinical studies can be carried out to assess the efficacy and safety of ezetimibe and interferon compared to interferon alone, as well as assessing ezetimibe in preventing infection in liver post-transplantation. It is expected that in each case, i.e., ezetimibe/interferon/ribavirin and ezetimibe/interferon, ezetimibe will enhance the clearance of the HCV infection as compared to interferon/ribavirin or interferon alone.

Example 6

Ezetimibe Does Not Inhibit HCV RNA Replication

HCV sg1b replicon cells or HCV sg2a replicon cells were vehicle-treated or treated with concentrations of ezetimibe (0, 7.5, 15, or 30 µM), G418 (500 µg/ml), Lovastatin (15 µM), or 2'-C-methylcytidine (12.5 µM) for 72 hours. Intracellular RNA was collected from triplicate wells at 12, 24, 48 and 72 hours post-treatment and HCV RNA was quantified by RT-qPCR, normalized to GAPDH. This analysis indicated that ezetimibe did not inhibit HCV subgenomic RNA replication.

Huh7 cultures were inoculated with HCVcc at an MOI of 0.01 FFU cell-1. Infected cultures were maintained for an additional 10 days to allow HCV RNA to reach steady-state levels. Cultures were then vehicle-treated, treated with ezetimibe (30 µM) or 2'-C-methylcytidine (12.5 µM). Fresh medium containing the specified treatments was replenished every day throughout the course of the experiment. Intracellular RNA was collected from triplicate wells at 24, 48, 72 and 96 hours post-treatment and HCV RNA was quantified by RT-qPCR and normalized to GAPDH. This analysis indicated that ezetimibe did not inhibit steady state HCVcc RNA levels.

Huh7 cultures were inoculated with HCVcc at an MOI of 0.01 FFU cell-1. Infected cultures were maintained for an additional 10 days to allow HCV RNA to reach steady-state levels. Cultures were then vehicle-treated, treated with ezetimibe (30 µM) or 2'-C-methylcytidine (12.5 µM). Fresh medium containing the specified treatments was replenished every day throughout the course of the experiment. HCVcc-containing supernatant was collected from triplicate wells at 24, 48, 72 and 96 hours post-treatment and HCV infectivity titers were determined. Infectivity titers are expressed as mean FFU/ml±SD for triplicate samples. This analysis indicated that ezetimibe did not inhibit secretion of infectious HCVcc.

Example 7

Ezetimibe Acts Synergistically with Protease Inhibitors

Figure 3:
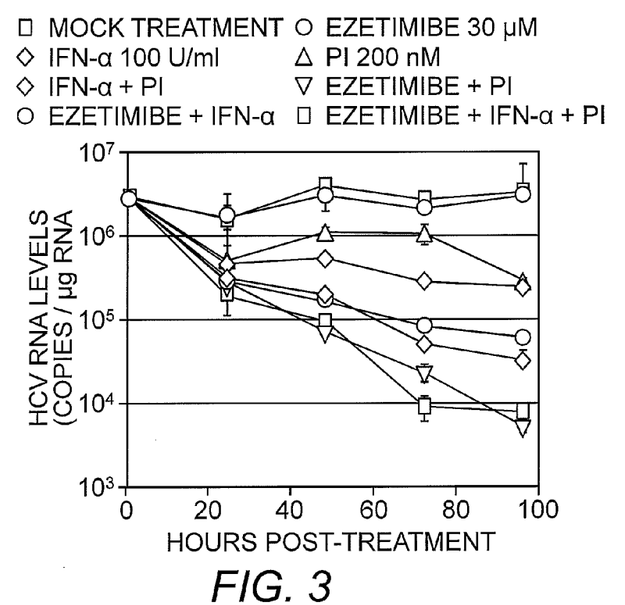
FIG. 3 shows that ezetimibe synergizes with IFN-α and protease inhibitors (PI) to potently inhibit chronic HCV infection. RT-qPCR analysis of intracellular HCV RNA levels in Huh7 cultures mock-treated, treated with ezetimibe (30 μM), PI (200 nM), IFN-α (100 U/ml), or indicated combinations thereof (n=3). Data presented are representative of multiple independent experiments.

As demonstrated herein, ezetimibe synergizes with interferon to reduce HCV levels in chronically infected cultures. However, IFN is often poorly tolerated and does not have a defined mode of action, thus the design of future IFN-free direct acting antiviral regimens is great interest. Therefore, the therapeutic potential of an IFN-free antiviral cocktail was also investigated, using ezetimibe in combination with other direct acting inhibitors of HCV amplification, specifically an inhibitor of the HCV NS3/4A protease (ITMN 5537; Intermune, Brisbane, Calif.). Huh7-1 cells were infected with HCV-JFH-1 and allowed to reach steady state levels of infection. Cells were monotreated with protease inhibitor (PI) or ezetimibe or IFN alone or treated with combinations of PI+ezetimibe or PI+IFN or IFN+ezetimibe or a combination of all three inhibitors. Samples were harvested at 24, 48, 72 or 96 hours post-treatment, the intracellular RNA was extracted and RT-qPCR performed to quantify HCV copies. This analysis indicated that the treatment with ezetimibe did not reduce HCV levels, while treatment with IFN or the PI alone reduced HCV levels by a log or less than a log, respectively (FIG. 3). Treatment with IFN+ezetimibe showed a synergistic effect reducing HCV by 2 logs (FIG. 3). However, the PI+ezetimibe combination reduced HCV levels by 2.5 logs and was as effective as the triple therapy with PI+IFN+ezetimibe. This demonstrates that ezetimibe can effectively synergize with direct acting inhibitors of HCV amplification.

This study demonstrates that an HCV entry/spread inhibitor (e.g., ezetimibe) greatly potentiates the effects of interferon or protease inhibitors. Apart from the obvious advantage that the addition of ezetimibe to HCV standard of care could significantly improve viral clearance rates, another notable advantage is that unlike current HCV direct acting antivirals that target virally-encoded proteins and are therefore prone to the emergence of viral escape mutants (Halfon & Locarnini (2011) *J. Hepatol.* 55(1):192-206); the likelihood that viral mutants resistant to ezetimibe will emerge is reduced as ezetimibe targets a host cell receptor rather than a specific viral protein. Thus, the addition of ezetimibe to multi-drug treatment regimens could increase the barrier of resistance to HCV direct acting antivirals by inhibiting the spread of direct acting antiviral-derived viral escape mutants in vivo.

Example 8

NPC1L1 is Required for HCV Cell-to-Cell Spread

Having demonstrated that NPC1L1 is required for cell-free HCV entry, the dependence of HCV cell-to-cell transmission on NPC1L1 was examined. Using an established antibody blocking approach (Timpe, et al. (2008) *Hepatology* 47:17-24), in which an antibody to the HCV E2 glycoprotein is used to block cell-free virus spread, the role of NPC1L1, CD81, or claudin-1 in cell-to-cell spread was tested. Briefly, subconfluent Huh7 cells were inoculated with HCVcc at a low multiplicity of infection (MOI) of 0.01 ffu/cell for 15 hours to allow sufficient time for initial viral entry into the primary cells (Sabahi, et al. (2010) *Virology* 407:110-9). Cells were then washed and cell-free virus spread was blocked by addition of an anti-E2 antibody at a concentration which neutralizes extracellular virus infection of cells. In parallel, cultures were co-treated with antibodies to CD81, Claudin-1 or NPC1L1 to determine if blocking of these factors prevents cell-to-cell spread. At seventy two hours post-infection, monolayers were fixed and stained for HCV-positive foci. Spread was determined by the size of the foci, as quantified by the number of cells per foci. Foci composed of 1-2 HCV E2-positive cells, which could have formed via cell division, were scored as infections that had not spread cell-to-cell, and are referred to as one-two cell foci, and represent a baseline for the assay. Foci containing 4 or more cells were scored as infections that had successfully spread cell-to-cell, and are referred to as multicellular foci. This analysis indicated that virtually all the foci formed in the cultures treated with either the irrelevant IgG control antibody or the HCV E2-specific antibody contained 4 or more HCV-positive cells confirming that HCV cell-to-cell spread was not affected by the presence of the anti-E2 antibody. Consistent with previous results (Witteveldt, et al. (2009) *J. Gen. Virol.* 90:48-58), it was observed that HCV cell-to-cell spread was only partially sensitive to the presence of the CD81 antibody at concentrations which inhibit cell-free virus infection such that 42% of foci still contained more than 4 HCV-positive cells, indicating that CD81-resistant routes of infection do exist. In contrast, the positive control claudin-1-specific antibody greatly inhibited HCV spread resulting in 94% of foci being restricted to 1-2 HCV-positive cells (Brimacombe, et al. (2011) *J. Virol.* 85:596-605). Notably, cell-to-cell HCV spread in the presence of antibody to NPC1L1 was inhibited to a similar extent as that of the anti-claudin-1 antibody.

Because an antibody to NPC1L1 loop 1 blocks cell-free virus infection, while an antibody to loop 2 is not effective in blocking infection, the ability of these antibodies to block cell-to-cell spread of the virus was examined. Analogous to the results obtained when assaying cell-free viral entry, it was observed that the antibody to loop 1 inhibited cell-to-cell HCV spread, causing 88% of the foci to be restricted to 1-2 cells, when compared to IgG control antibody-treated cells, while the antibody to loop 2 only resulted in 30% of the foci to be restricted to one-two cells.

Example 9

NPC1L1-Mediated Cell-to-Cell Spread as an Effective Anti-HCV Therapeutic Target

It has now been shown that ezetimibe, which blocks NPC1L1 internalization, inhibits HCV infection initiation in cultured cells and in chimeric mice transplanted with human hepatocytes. To confirm the role of NPC1L1 in HCV spread and verify that ezetimibe inhibits HCV cell-to-cell spread, Huh7-1 cells were inoculated with HCV JFH-1 at an MOI of 0.01 for 16 hours to allow cell-free entry to initiate infection in a small percentage of cells, before being washed and then incubated with increasing concentrations of ezetimibe. Once again extracellular HCV entry was blocked by the addition of anti-E2 antibody to neutralize cell-free virus in all cultures. The results of this analysis indicated that while this inhibitor blocks HCV entry, addition of ezetimibe post-infection did not block infection of naïve Huh7 cells as determined by the number of independent infection initiation events (i.e., foci of 1-2 E2-positive cells) by 24 hours post-infection, a time at which HCV has completed only one round of its life cycle. Cells were fixed at 72 hours post-infection, and then stained to detect the number and the size of the E2-positive foci. The foci were counted and scored as one-two cell foci or as multicellular foci. Consistent with the conclusion that NPC1L1 is required for HCV cell-to-cell spread, a dose-dependent inhibition in the size of the E2-positive foci formed was observed in the presence of ezetimibe. The same 30 µM dose of ezetimibe previously shown to block cell-free virus infection of cells when added prior to viral inoculation, resulted in foci of 1-2 cells when added post-viral inoculation while the lower doses resulted in a successively larger proportion of the foci composed of four or more infected cells. To ensure that multicellular foci were not a result of cell division over the time course of the experiment, the same experiment was repeated in non-growing Huh7-1 cells and similar results were obtained.

To determine if ezetimibe might be an effective therapeutic for inhibiting HCV spread of other HCV genotypes, intergenotypic HCVcc chimeras were used, in which the core through E2 region of the JFH-1 clone had been replaced with analogous regions of various HCV genotypes including H77C, J4, J8, ED43, SA13, HK6A and QC69 (Gottwein, et al. (2009) *Hepatology* 49(2):364-77). Again, to avoid issues of cell division, non-growing Huh7-1 cells were infected with the different chimeric viruses, and after 16 hours, the cells were washed and 0 µM or 30 µM ezetimibe was added to parallel cultures. Since the chimeras encode unique E2 proteins and thus may have differing sensitivity to inhibition by the anti-E2 antibody, in this experiment methyl cellulose was added to all cultures as an alternative means of minimizing cell-free virus spread. Seventy-two hours post-infection, the cells were fixed and stained with an antibody to HCV NS5A to detect the size of the foci formed. In all cases, the size of foci formed by each chimera were reduced in the presence of ezetimibe relative to the mock-treated control culture confirming not only that all of these genotypes use the NPC1L1 receptor for cell-to-cell spread, but that the spread of all the chimeric viruses can be inhibited by ezetimibe.

Example 10

Inhibition of the VLDL Pathway Prevents Secretion of Cell-Free Virus

Because HCV cell-free spread requires the production and secretion of infectious viral particles from infected cells, an alternative way to block cell-free virus spread is to prevent the release of infectious virus from already infected cells. Relevant to this, it has been demonstrated that infectious HCV particles are lipidated and released from cells via the VLDL secretory pathway and that inhibition of this cellular pathway in turn inhibits secretion of infectious HCV from cells (Huang, et al. (2007) *Proc. Natl. Acad. Sci. USA* 104:5848-53; Gastaminza, et al. (2008) *J. Virol.* 82:2120-9; Nahmias, et al. (2008) *Hepatology* 47:1437-45). In particular, the flavonoid extract, naringenin has been shown to inhibit MTP (microsomal transfer protein) activity, thereby decreasing ApoB secretion and consequently inhibiting HCV particle secretion (Nahmias, et al. (2008) supra; Goldwasser, et al. (2011) *J. Hepatol.* 55:963-71). It was of interest to determine whether the VLDL secretory pathway and related virion lipid modifications are required for cell-to-cell spread. Therefore, naringenin was used to inhibit HCV particle maturation through the ApoB-dependent VLDL secretory pathway and its effect on the cell-to-cell spread of intracellular HCV particles was examined using a foci-size assay. Non-growing Huh7-1 cells were infected with HCV-JFH-1 at an MOI of 0.01. After 15 hours, naringenin or vehicle was added to the infected cell monolayers at a concentration that inhibits virus particle secretion by 80-900 (Nahmias, et al. (2008) supra; Goldwasser, et al. (2011) supra). Anti-E2 antibodies were added at a concentration to neutralize extracellular virus. Drug and antibodies were replenished every 3 days. Five days post-infection, the cells were fixed and stained to detect the size and morphology of the HCV-positive cell foci. It was observed that the number and size of the foci in the wells treated with naringenin were similar to that observed in the cultures treated with the vehicle. Therefore, while the presence of naringenin inhibits the secretion of infectious HCV particles into the extracellular medium, inhibition of cell-tocell spread was not detected when compared to the vehicle control, suggesting that the process of HCV cell-to-cell spread is independent or has little dependence on the VLDL secretory pathway, and that VLDL inhibitors may have limited utility for preventing viral spread clinically.

To determine if naringenin affects spread of any of the other HCV genotypes, non-growing Huh7-1 cells were infected with the different intergenic chimeric viruses and after 16 hours, the cells were washed and naringenin was added. Methyl cellulose was added to each well to prevent cell-free virus spread. In parallel, a control set of wells was treated with methyl cellulose alone. Five days post-infection, the cells were fixed and stained to detect the number of HCV NS5A-positive cells. For all chimeric viruses, except for the J8/JFH-1 (2B/JFH-1) chimera, the number of HCV-positive cells in the foci observed in the naringenin-treated samples was similar to that observed in the control wells treated with methyl cellulose alone indicating that cell-to-cell spread of the virus was not inhibited by naringenin. Notably, however, the foci in the wells treated with naringenin tended to be more compact than in the control wells overlaid with methyl cellulose alone, suggesting that perhaps the methyl cellulose is not as effective at preventing local cell-free virus spread as naringenin. The one exception was the J8/JFH-1 chimera, which consistently produced smaller foci even in mock-treated cells indicating that this chimeric virus inherently does not spread efficiently by cell-to-cell transmission. Additionally, the presence of naringenin reduced the size of foci formed by the virus indicating that unlike all the other viruses screened, the spread of this particular chimeric virus may be dependent on the VLDL pathway.

To determine the nature of the intracellular JFH-1 virion particles which are able to spread from cell-to-cell, even in the absence of secretion, the buoyant density of the accumulated, intracellular particles from naringenin-treated cells were analyzed on iodixanol gradients. It was observed that the peak of RNA from these cells was shifted towards the heavier fractions consistent with the intracellular particles in naringenin-treated cells being less lipidated. Infectivity of the intracellular virus from naringenin-treated cells was reduced by more than 95% in a standard cell-free virus infection of naïve Huh7-1 cells. It was therefore concluded that naringenin treatment caused HCV particles to be less lipidated, but that these less lipidated particles are capable spreading cell-to-cell via a VLDL-independent pathway Example 11

Analysis of Entry/Egress Inhibitors in Combination with Ezetimibe

The use of an entry inhibitor or an egress inhibitor alone may be of limited use in patients with chronic HCV infections, since many target cells are already infected. However, these inhibitors might significantly enhance viral clearance when used in combination with antivirals that reduce intracellular HCV amplification (e.g., interferon, protease inhibitors, or polymerase inhibitors). Such a combination could prevent infection of new target cells and protect cells cleared of HCV from re-infection. Moreover, the combination of agents would also more specifically prevent the spread of viral escape mutants which commonly arise during treatment with direct acting agents. As demonstrated herein, ezetimibe synergizes with interferon to inhibit chronic HCV infection. Moreover, given that ezetimibe also blocks cell-to-cell mediated entry of HCV into secondary target cells, it was of interest to determine whether the synergy observed between ezetimibe and interferon was specifically dependent on the ability of ezetimibe to block cell-to-cell spread.

Figure 4A:
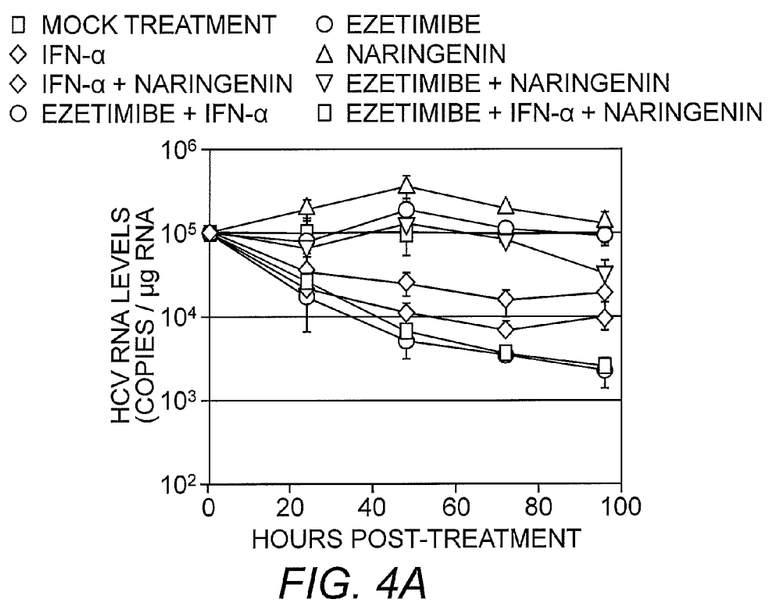
FIG. 4 shows the effect of HCV inhibitor combinations on chronic HCV infection.

To demonstrate this, the synergy potential of IFN-α and the secretion inhibitor naringenin were examined. Like ezetimibe, naringenin would be expected to block cell-free HCV infection, but unlike ezetimibe does not prevent cell-to-cell spread of the virus. Thus, parallel cultures of chronically infected Huh7-1 cells were established and subsequently treated with ezetimibe, naringenin or IFN-α, either alone or in combination. Treatments were replenished every 24 hours. Triplicate cultures of each treatment condition were harvested at 24, 48, 72 or 96 hours post-treatment and intracellular HCV levels were quantified by RT-qPCR (FIG. 4A). This analysis indicated that treatment with ezetimibe alone did not reduce HCV levels in chronically infected cultures, while treatment with IFN-α alone resulted in a log decrease in HCV copies. However, combination treatment with IFN-α and ezetimibe resulted in a synergistic 1.5 log reduction of HCV copies. Interestingly, blocking cell-free spread with naringenin actually increased intracellular HCV copies by about 50%, most likely due to inhibition of secretion causing an accumulation of intracellular HCV particles. Similarly, combination treatment with IFN-α and naringenin resulted in higher intracellular HCV levels compared to treatment with IFN-α alone. Thus, no evidence of synergy was observed when IFN-α was combined with an egress inhibitor that only blocks cell-free spread. Lastly, when included as part of a triple treatment combination with ezetimibe and IFN-α, naringenin did not enhance viral clearance; consistent with the fact that ezetimibe already effectively blocks cell-free HCV spread.

Figure 4B:
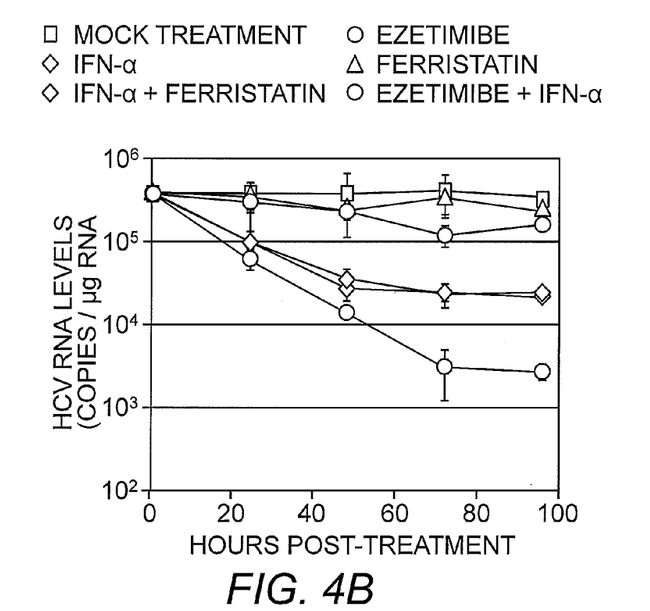

As an alternative method of determining the therapeutic importance of inhibiting HCV cell-to-cell spread, an inhibitor to TfR1 was used. TfR1 has also been identified as another host cell factor that is involved in cell-free entry of HCV into cells, but is not required for cell-to-cell-mediated HCV entry. Thus, unlike ezetimibe which inhibits both cell-free and cell-to-cell HCV spread, the TfR1 inhibitor, ferristatin, only blocks cell-free virus spread. Again, chronically infected Huh7-1 cell cultures were established and treated with ezetimibe (30 µM), ferristatin (50 µM), or IFN-α (100 U/ml), either alone or in combination and treatments were replenished every 24 hours. Intracellular HCV copies were quantified from triplicate cultures by RT-qPCR at 24, 48, 72 or 96 hours post-treatment (FIG. 4B). This analysis indicated that neither ezetimibe nor ferristatin alone reduced intracellular HCV load in chronically infected cultures, while cells treated with IFN-α resulted in a log decrease in HCV levels. Importantly, although cells treated with both IFN-α and ezetimibe showed a 1.5 log decrease in intracellular HCV load, combination treatment with IFN-α and ferristatin had intracellular HCV load similar to cells treated with IFN-α alone. Therefore, analogous to what was observed with naringenin, combination treatment with IFN plus an entry inhibitor that only blocks cell-free virus entry exhibited no synergistic reduction of HCV infection.

This data indicates that only specific combinations of inhibitors can synergistically reduce HCV levels. Specifically, entry and egress inhibitors that block both cell-free and cell-to-cell HCV entry into naïve cells exhibit synergy when used in combination with antivirals that reduce HCV intracellular production.

Example 12

Ezetimibe Acts Synergistically with Polymerase Inhibitors

Figure 5:
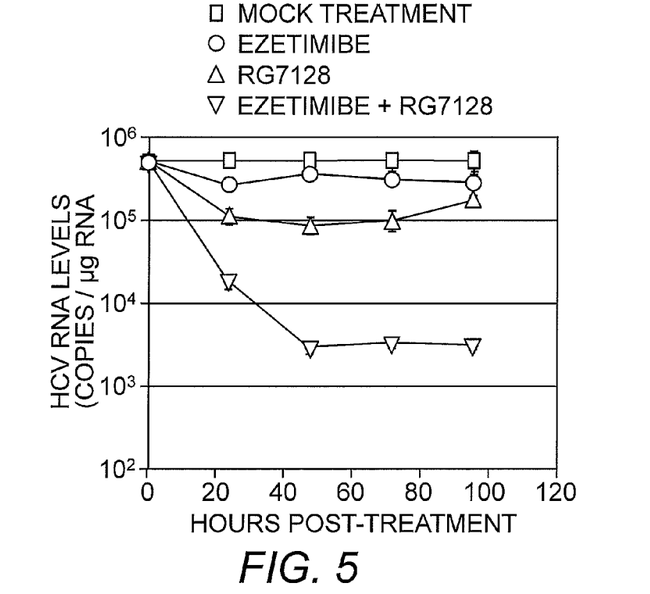
FIG. 5 shows that ezetimibe synergizes with an HCV polymerase inhibitor to potently inhibit chronic HCV infection. Shown are the results of RT-qPCR analysis of intracellular HCV RNA levels in Huh7 cultures mock-treated, treated with ezetimibe (30 μM), polymerase inhibitor, RG7128 (1 μM), or a combination thereof (n=3).

Huh7-1 cells were infected with HCV-JFH-1 and allowed to reach steady state levels of infection. Cells were monotreated with HCV polymerase inhibitor RG7128 (1 µM)

or ezetimibe (30 μM) alone or treated with a combination of RG7128 and ezetimibe. Samples were harvested at 24, 48, 72 or 96 hours post-treatment, the intracellular RNA was extracted, RT-qPCR was performed to quantify HCV copies, and the data was normalized to Mock treatment (FIG. 5). This analysis indicated that the treatment with ezetimibe did not reduce HCV levels, while treatment with RG7128 alone reduced HCV levels by less than a log (FIG. 5). However, treatment with RG7128 and ezetimibe showed a synergistic effect reducing HCV by 2 logs (FIG. 5). This demonstrates that ezetimibe can effectively synergize with direct acting inhibitors of HCV polymerase.

What is claimed is:

1. A synergistic composition for treating a hepatic virus infection comprising a Niemann-Pick C1-like 1 protein antagonist and at least one other agent that inhibits hepatic virus infection, wherein the at least one other agent that inhibits hepatic virus infection comprises a type I interferon, a hepatic virus protease inhibitor, a hepatic virus polymerase inhibitor, a nucleoside inhibitor, or a hepatic virus replication inhibitor, with the proviso that the other agent is not simvastatin.

2. The synergistic composition of claim 1, wherein the Niemann-Pick C1-like 1 protein antagonist is an azetidinone-based cholesterol absorption inhibitor.

3. The synergistic composition of claim 2, wherein the azetidinone-based cholesterol absorption inhibitor is ezetimibe, or a derivative thereof.

4. The synergistic composition of claim 1, further comprising a pharmaceutically acceptable carrier.

5. The synergistic composition of claim 1, wherein the hepatic virus replication inhibitor is a NS4B protein inhibitor or a NS5A protein inhibitor.

* * * * *

```
                          SEQUENCE LISTING

<160> NUMBER OF SEQ ID NOS: 6

<210> SEQ ID NO 1
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 1
gaaggtgaag gtcggagtc                                                  19

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
gaagatggtg atgggatttc                                                 20

<210> SEQ ID NO 3
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 3
tctgcggaac cggtgagta                                                  19

<210> SEQ ID NO 4
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 4
tcaggcagta ccacaaggc                                                  19

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
gcctagccat ggcgttagta                                                 20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 6
ctcccggggc actcgcaagc                                                        20
```